US00PP14631P29

(12) United States Plant Patent
Oudshoorn

(10) Patent No.: US PP14,631 P2
(45) Date of Patent: Mar. 23, 2004

(54) PAPAVER PLANT NAMED 'PAPILLON'

(50) Latin Name: *Papaver orientale*
Varietal Denomination: Papillon

(75) Inventor: Hubertus Gerardus Oudshoorn, Rijpwetering (NL)

(73) Assignee: Future Plants V.O.F., Lisserbroek (NL)

( * ) Notice: Subject to any disclaimer, the term of this patent is extended or adjusted under 35 U.S.C. 154(b) by 0 days.

(21) Appl. No.: 10/437,954

(22) Filed: May 13, 2003

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,712 P2 * 6/2002 Oudshoorn ..... Plt./263

OTHER PUBLICATIONS

UPOV–ROM GTITM Computer Database, GTI Jouve Retrieval Software 2003/04 Citation(s) for 'Papillon'.*

* cited by examiner

*Primary Examiner*—Bruce R. Campell
*Assistant Examiner*—W C Haas
(74) *Attorney, Agent, or Firm*—C. A. Whealy

(57) ABSTRACT

A distinct cultivar of Papaver plant named 'Papillon', characterized by its upright and relatively compact plant habit; moderately vigorous growth habit; and flowers with light purple-colored petals.

2 Drawing Sheets

Botanical classification/cultivar designation: *Papaver orientale* cultivar Papillon.

BACKGROUND OF THE INVENTION

The present Invention relates to a new and distinct cultivar of Papaver plant, botanically known as *Papaver orientale*, commercially referred to as Oriental Poppy, and hereinafter referred to by the cultivar name Papillon.

The new Papaver is a product of a planned breeding program conducted by the Inventor in Rijpwetering, The Netherlands. The objective of the breeding program is to develop new Papaver cultivars with compact plant habit. The new Papaver originated from a cross-pollination made by the Inventor of two unidentified selections of *Papaver orientale*, not patented. The new Papaver was discovered and selected by the Inventor in 2000 in a controlled environment in Rijpwetering, The Netherlands, from the resultant progeny of the cross-pollination on the basis of its compact plant habit.

Asexual reproduction of the new cultivar by cuttings taken at Rijpwetering, The Netherlands, has shown that the unique features of this new Papaver are stable and reproduced true to type in successive generations.

SUMMARY OF THE INVENTION

Plants of the cultivar Papillon have not been observed under all possible environmental conditions. The phenotype may vary somewhat with variations in environment such as temperature and light intensity without, however, any variance in genotype.

The following traits have been repeatedly observed and are determined to be the unique characteristics of 'Papillon'. These characteristics in combination distinguish 'Papillon' as a new and distinct Papaver cultivar:

1. Upright and relatively compact plant habit.
2. Moderately vigorous growth habit.
3. Flowers with light purple-colored petals.

Plants of the cultivar Papillon differ from plants of the parent selections and other Papaver cultivars known to the Inventor, such as the cultivar Patty's Plum, not patented, in plant height as plants of the new Papaver are more compact than plants of the parent selections and other cultivars known to the Inventor.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new Papaver.

The photograph at the top of the first sheet comprises a side perspective view of typical flowering plants of 'Papillon' grown in an outdoor nursery.

The photograph at the top of the second sheet is a close-up view of a typical flower of 'Papillon'.

The photograph at the bottom of the second sheet is a close-up view of a typical leaf of 'Papillon'.

DETAILED BOTANICAL DESCRIPTION

In the following description, color references are made to The Royal Horticultural Society Colour Chart, 2001 Edition, except where general terms of ordinary dictionary significance are used. Plants used for the abovementioned photographs and following observations and measurements were grown in an outdoor nursery in Roelofarendsveen, The Netherlands, and under conditions which closely approximate commercial production conditions during the summer. The photographs, measurements and observations were taken during July when the plants were about one year old. During this time, day temperatures ranged from 14 to 27° C. and night temperatures ranged from 4 to 16° C.

Botanical classification: *Papaver orientale* L. cultivar Papillon.

Parentage:

*Female, or seed, parent.*—Unidentified selection of *Papaver orientale*, not patented.

*Male, or pollen, parent.*—Unidentified selection of *Papaver orientale*, not patented.

Propagation:

*Type.*—By cuttings.

*Time to develop roots.*—About 90 days at 18° C.

*Root description.*—Fleshy, thick; light brown to white in color.

Plant description:

*Form.*—Herbaceous perennial flowering plant; mostly upright; narrow inverted triangle. Basally branching, rosette; flowering stems arise from the base. Moderately vigorous.

*Plant height.*—About 75 cm.

*Plant diameter.*—About 40 cm.

*Flowering stems (peduncles).*—Length: About 75 cm. Diameter: About 5 mm. Internode length: About 18 cm. Strength: Strong. Aspect: Erect. Texture: Pubescent; rough. Color: 143A.

*Foliage description.*—Arrangement: Alternate; simple. Shape: Lanceolate, pinnately and deeply dissected. Length: About 39.7 cm. Width: About 12.4 cm. Leaf segment shape: Lanceolate. Leaf segment apex: Acute. Leaf segment base: Cuneate. Leaf segment margin: Lower half, pinnatisect to pinnatifid; upper half, biserrate and serrate. Texture, upper and lower surfaces: Pubescent; very rough. Venation pattern: Pinnate. Color: Developing foliage, upper surface: 143A. Developing foliage, lower surface: 137C. Fully expanded foliage, upper surface: Slightly darker than 143A. Fully expanded foliage, lower surface: 138A to 138B. Venation, upper surface: 144A. Venation, lower surface: 138C. Petioles: Length: Basal leaves, about 10 cm; stem leaves, about 1 cm. Diameter: About 7.5 mm. Color: 138C.

Flower description:

*Flower type and habit.*—Single rotate flowers; flowers terminal and face mostly upright. Flowers not persistent. One flower per flowering stem.

*Natural flowering season.*—Plants flower continuously from June to early July in The Netherlands.

*Fragrance.*—None detected.

*Flower longevity on the plant.*—About three days.

*Flower size.*—Diameter: About 10.8 cm. Depth (height): About 6.8 cm.

*Flower buds.*—Length: About 3.3 cm. Diameter: About 1.1 cm. Shape: Ovoid. Texture: Pubescent; rough. Color: 200B to 200C; towards the base, 137B to 137C.

*Petals.*—Arrangement/appearance: Rotate; about six petals forming a cup-shaped corolla. Length: About 7.6 cm. Width: About 7.6 cm. Shape: Obcordate. Apex: Retuse; ruffled. Margin: Entire; ruffled. Texture, upper and lower surfaces: Smooth; glabrous. Color: When opening and fully opened, upper surface: 186D; towards the base, 59A to 187B; basal spot, close to 202A. When opening and fully opened, lower surface: 186D; towards the base, 60C. Fully opened, upper surface: 40A; towards the base, 187A; basal spot, close to 202A. Fully opened, lower surface: 40B; towards the base, 187A; basal spot, close to 202A.

*Sepals.*—Sepal development has not been observed.

*Reproductive organs.*—Stamens: Quantity per flower: Numerous, typically about 300. Anther shape: Narrowly oblong; basifixed; occasionally curved. Anther length: About 2 mm. Anther color: 59A to 187A to 187B. Filament length: About 1.5 cm. Pollen amount: Scarce. Pollen color: Close to 202B. Pistils: Quantity per flower: About 12. Pistil length: About 8 mm. Stigma shape: Narrowly oblong. Stigma color: Between N186A and 202A. Ovary color: 143A to 143B.

*Fruits.*—Quantity per flower: One. Type: Capsule. Length: About 3.2 cm. Diameter: About 2.9 cm. Color: N200A.

*Seeds.*—Quantity per fruit: About 900. Length: About 1 mm. Diameter: About 1 mm. Color: Between 202A and 202B.

Disease/pest resistance: Plants of the new Papaver have not been noted to be resistant to pathogens and pests common to Papaver.

Temperature tolerance: Plants of the new Papaver have been observed to tolerate temperatures from −30 to 40° C.

It is claimed:

1. A new and distinct cultivar of Papaver plant named 'Papillon', as illustrated and described.

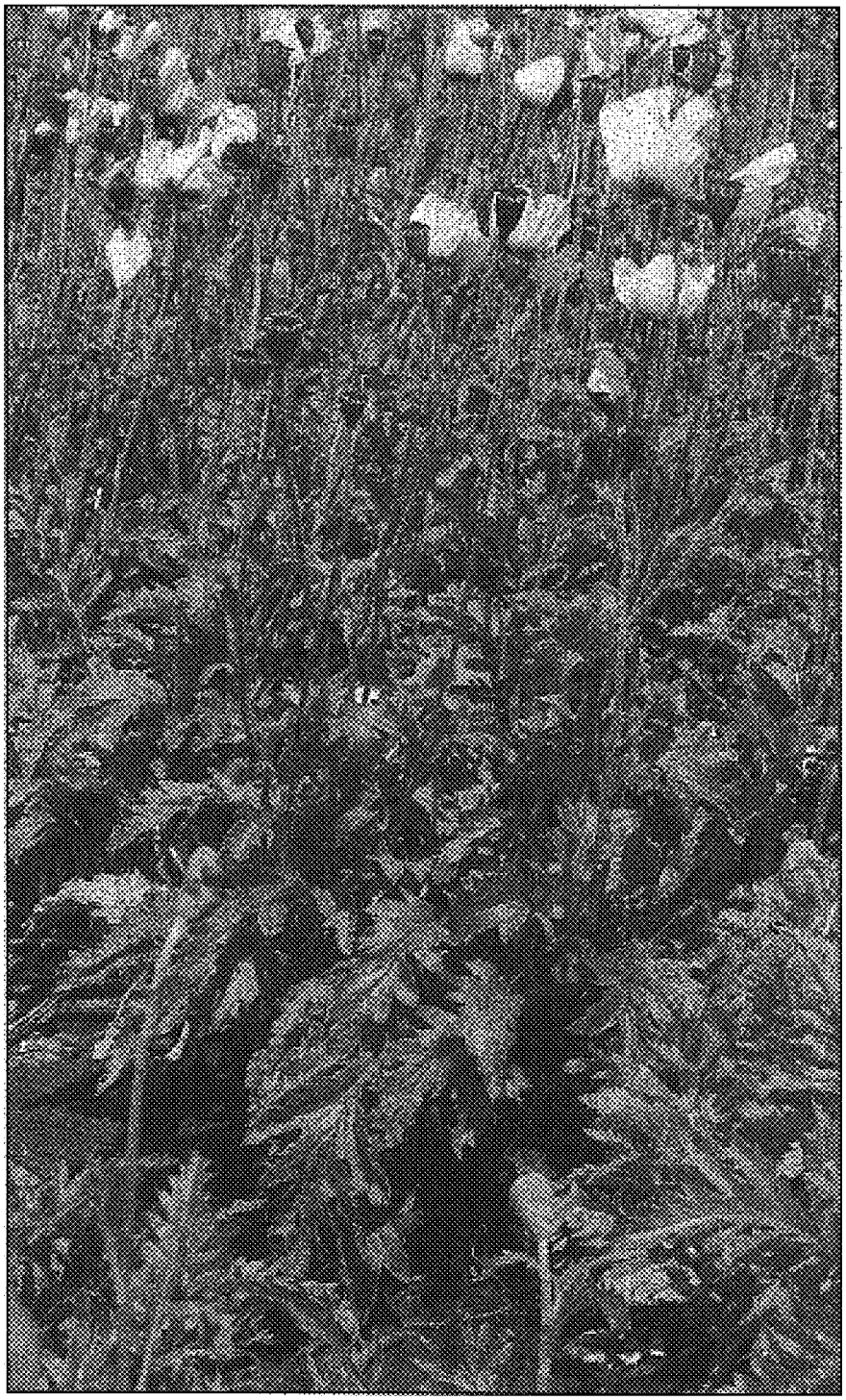

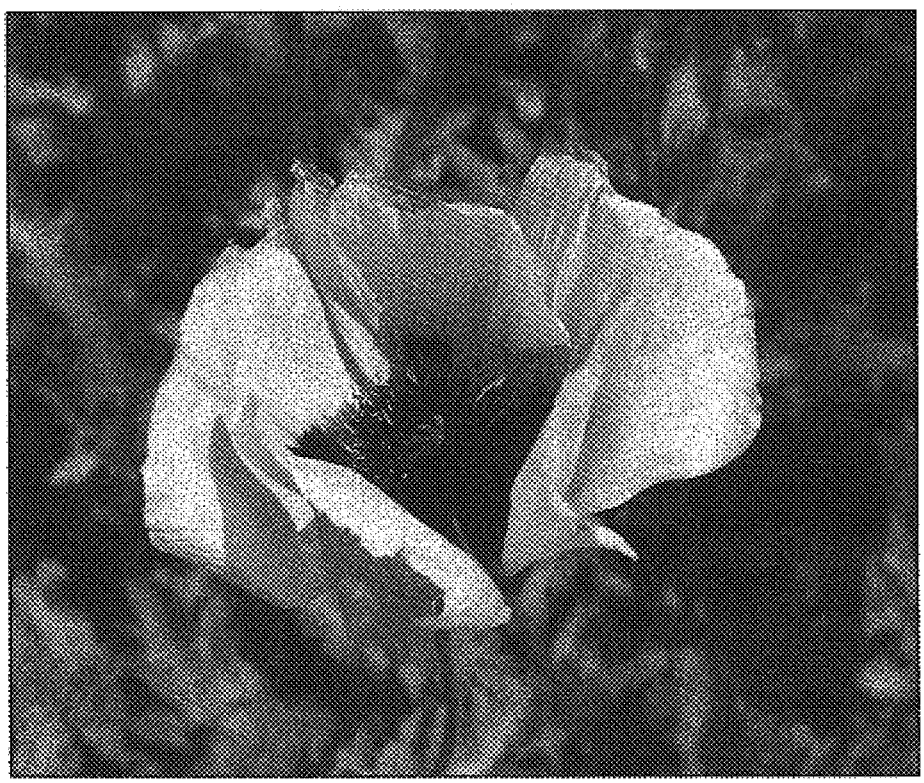
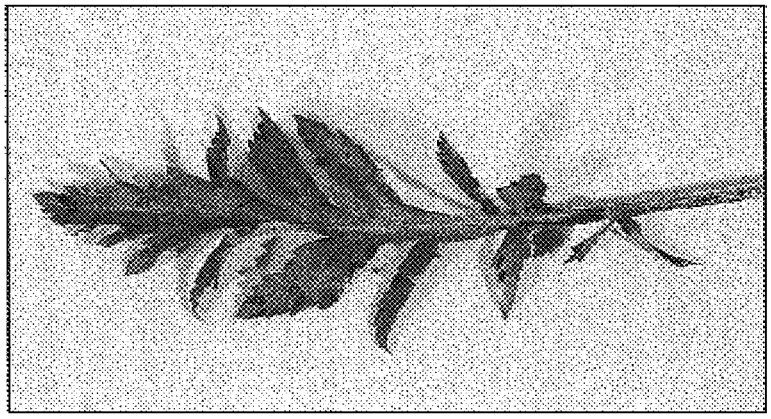

* * * * *